(12) United States Patent
Barth et al.

(10) Patent No.: US 7,294,645 B2
(45) Date of Patent: Nov. 13, 2007

(54) DERIVATIVES OF N'-(1,5-DIPHENYL-1H-PYRAZOL-3-YL) SULFONAMIDE WITH CB1 RECEPTOR AFFINITY

(75) Inventors: Francis Barth, Saint Georges d'Orques (FR); Serge Martinez, Montpellier (FR); Murielle Rinaldi-Carmona, Saint Georges d'Orques (FR); Christian Congy, Saint Gely du Fesc (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 11/428,928

(22) Filed: Jul. 6, 2006

(65) Prior Publication Data

US 2007/0021486 A1  Jan. 25, 2007

Related U.S. Application Data

(63) Continuation of application No. PCT/FR2005/000031, filed on Jan. 7, 2005.

(30) Foreign Application Priority Data

Jan. 12, 2004 (FR) .................... 04 00257

(51) Int. Cl.
*A61K 31/415* (2006.01)
*C07D 231/10* (2006.01)

(52) U.S. Cl. ................ 514/406; 548/356.1; 548/373.1; 548/375.1; 514/403

(58) Field of Classification Search ............. 548/356.1, 548/373.1, 375.1; 514/403, 406
See application file for complete search history.

(56) References Cited

FOREIGN PATENT DOCUMENTS

EP   0576357   12/1993

*Primary Examiner*—Golam M. M. Shameem
(74) *Attorney, Agent, or Firm*—Balaram Gupta

(57) ABSTRACT

The invention relates to compounds of formula (I):

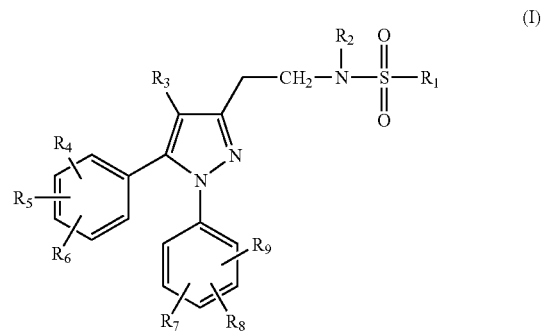

Wherein $R_1$, $R_2$, $R_3$, $R_4$, $R_5$, $R_6$, $R_7$, $R_8$, $R_9$ are as defined herein. The invention also relates to the preparation method thereof and to the use of same in therapeutics.

6 Claims, No Drawings

DERIVATIVES OF N'-(1,5-DIPHENYL-1H-PYRAZOL-3-YL) SULFONAMIDE WITH CB1 RECEPTOR AFFINITY

CROSS REFERENCE TO RELATED APPLICATIONS

This application is a continuation of International application No. PCT/FR2005/000,031, filed Jan. 7, 2005, which is incorporated herein by reference in its entirety; which claims the benefit of priority of French Patent Application No. 04/00,257, Jan. 12, 2004.

BACKGROUND OF THE INVENTION

1. Field of the Invention

The subjection of the present invention is N-[(1,5-diphenyl-1H-pyrazol-3-yl)methyl]sulfonamide derivatives, their preparation and their therapeutic application.

2. Description of the Art

Diphenylpyrazole derivatives having affinity for the $CB_1$ cannabinoid receptors have been described in particular in patents EP 0 576 357, EP 0 656 354 and U.S. Pat. No. 5,624,941. All of these references are incorporated herein by reference in their entirety.

Novel N-[(1,5-diphenyl-1H-pyrazol-3-yl)methyl]sulfonamide derivatives which possess $CB_1$ cannabinoid receptor antagonist properties have now been found.

SUMMARY OF THE INVENTION

The subject of the present invention is compounds corresponding to the formula (I):

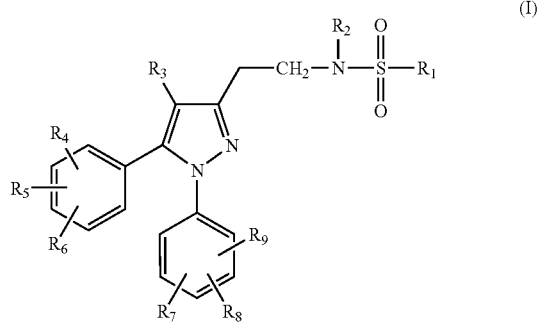

in which:

$R_1$ represents
- a $(C_1-C_6)$alkyl;
- a $(C_3-C_7)$cycloalkyl which is unsubstituted or substituted once or several times with a $(C_1-C_3)$alkyl group;
- a $(C_3-C_7)$cycloalkylmethyl which is unsubstituted or substituted once or several times on the carbocycle with a $(C_1-C_3)$alkyl;
- a phenyl which is unsubstituted or mono-, di- or trisubstituted with a substituent independently chosen from a halogen atom, a $(C_1-C_4)$alkyl, a $(C_1-C_3)$alkoxy, a cyano, a trifluoromethyl radical, a trifluoromethoxy radical, an $S(O)_n$Alk group, a $(C_1-C_3)$alkylcarbonyl group, a phenyl;
- a benzyl which is unsubstituted or mono- or disubstituted with a substituent independently chosen from a halogen atom, a $(C_1-C_3)$alkyl, a $(C_1-C_3)$alkoxy; a trifluoromethyl radical;
- a thienyl which is unsubstituted or substituted with a halogen atom or with an isoxazolyl;

$R_2$ represents a hydrogen atom or a $(C_1-C_3)$alkyl;

$R_3$ represents a hydrogen atom or a $(C_1-C_5)$alkyl;

$R_4$, $R_5$, $R_6$, $R_7$, $R_8$ and $R_9$ each independently represent a hydrogen atom, a halogen atom, a $(C_1-C_7)$alkyl, a $(C_1-C_5)$alkoxy, a trifluoromethyl radical or an $S(O)_n$Alk group;

n represents 0, 1 or 2;

Alk represents a $(C_1-C_4)$alkyl.

The compounds of formula (I) may contain one or more asymmetric carbon atoms. They can therefore exist in the form of enantiomers or diastereoisomers. These enantiomers, diastereoisomers and mixtures thereof, including the racemic mixtures, form part of the invention.

The compounds of formula (I) may exist in the form of bases or addition salts with acids. Such addition salts form part of the invention.

These salts are advantageously prepared with pharmaceutically acceptable acids but the salts of other acids useful for the purification or isolation of the compounds of formula (I) also form part of the invention.

The compounds of formula (I) may also exist in the form of hydrates or solvates, namely in the form of associations or combinations with one or more molecules of water or with a solvent. Such hydrates and solvates also form part of the invention.

DETAILED DESCRIPTION OF THE INVENTION

The expression halogen atom is understood to mean a bromine, chlorine, fluorine or iodine atom.

The expression $(C_1-C_3)$alkyl or respectively $(C_1-C_4)$alkyl, $(C_1-C_5)$alkyl, $(C_1-C_6)$alkyl or $(C_1-C_7)$alkyl is understood to mean a linear or branched alkyl radical of one to three carbon atoms or respectively of one to four carbon atoms, of one to five carbon atoms, of one to six carbon atoms or of one to seven carbon atoms, such as the methyl, ethyl, propyl, isopropyl, butyl, isobutyl, sec-butyl, tert-butyl, pentyl, isopentyl, hexyl, isohexyl or heptyl radical.

The expression $(C_1-C_3)$alkoxy or respectively $(C_1-C_5)$alkoxy is understood to mean a linear or branched alkoxy radical of one to three carbon atoms or respectively of one to five carbon atoms, such as the methoxy, ethoxy, propoxy, isopropoxy, butoxy, sec-butoxy, tert-butoxy, pentoxy or isopentoxy radical.

The expression $(C_3-C_7)$cycloalkyl is understood to mean a cyclic alkyl group of 3 to 7 carbon atoms, such as the cyclopropyl, cyclobutyl, cyclopentyl, cyclohexyl or cycloheptyl group.

Among the compounds of formula (I), which are the subject of the invention, there may be mentioned the preferred compounds which are defined as follows:

$R_1$ represents
- an ethyl, an isopropyl, an n-butyl;
- a cyclohexyl;
- a cyclohexylmethyl;
- a 2-chlorophenyl, a 3-chlorophenyl, a 2-fluoro-phenyl, a 3-chloro-4-fluorophenyl, a 4-bromo-2-ethylphenyl, a 3-methylphenyl, a 4-tert-butylphenyl, a 3,5-dimethylphenyl, a 3-methoxy-phenyl, a 4-methoxyphenyl, a 3-cyanophenyl, a 4-cyanophenyl, a 2-(trifluoromethyl)phenyl, a 3-(trifluoromethyl)phenyl, a 4-(trifluoro-methyl)phenyl, a 3,5-bis(trifluoromethyl)-phenyl, a 2-(trifluoromethoxy)phenyl, a 3-(trifluoromethoxy)phenyl, a 2-(methylsulfonyl)-phenyl, a 3-(methylsulfonyl)phenyl, a 3-acetylphenyl, a 3-biphenyl, a 2-biphenyl;

a 3-chlorobenzyl, a 2-fluorobenzyl, a 4-fluoro-benzyl, a 3-(trifluoromethyl)benzyl, a 4-(tri-fluoromethyl)benzyl;

a 5-bromo-2-thienyl; a 5-isoxazol-3-yl-2-thienyl;

and/or $R_2$ represents a hydrogen atom or a methyl;

and/or $R_3$ represents a methyl or an ethyl;

and/or $R_4$ represents a hydrogen atom;

and/or $R_5$ is at the 4-position of the phenyl and represents a bromine, chlorine or fluorine atom, or a methoxy;

and/or $R_6$ represents a hydrogen atom;

and/or $R_7$ represents a hydrogen atom;

and/or $R_8$ is at the 4-position of the phenyl and represents a hydrogen atom, a chlorine atom, a fluorine atom;

and/or $R_9$ is at the 2-position of the phenyl and represents a chlorine or fluorine atom;

in the form of a base or of an addition salt with an acid, and in the form of a hydrate or a solvate.

Among the latter preferred compounds, those particularly preferred are the compounds of formula (I) for which:

$R_1$ represents
 an ethyl, an isopropyl, an n-butyl;
 a cyclohexyl;
 a cyclohexylmethyl;
 a 2-chlorophenyl, a 3-chlorophenyl, a 2-fluoro-phenyl, a 3-chloro-4-fluorophenyl, a 4-bromo-2-ethylphenyl, a 3-methylphenyl, a 4-tert-butyl-phenyl, a 3,5-dimethylphenyl, a 3-methoxy-phenyl, a 4-methoxyphenyl, a 3-cyanophenyl, a 4-cyanophenyl, a 2-(trifluoromethyl)phenyl, a 3-(trifluoromethyl)phenyl, a 4-(trifluoro-methyl)phenyl, a 3,5-bis(trifluoromethyl)-phenyl, a 2-(trifluoromethoxy)phenyl, a 3-(trifluoromethoxy)phenyl, a 2-(methylsulfonyl)-phenyl, a 3-(methylsulfonyl)phenyl, a 3-acetylphenyl, a 3-biphenyl, a 2-biphenyl;
 a 3-chlorobenzyl, a 2-fluorobenzyl, a 4-fluoro-benzyl, a 3-(trifluoromethyl)benzyl, a 4-(trifluoromethyl)benzyl;
 a 5-bromo-2-thienyl; a 5-isoxazol-3-yl-2-thienyl;

$R_2$ represents a hydrogen atom or a methyl;

$R_3$ represents a methyl or an ethyl;

$R_4$ represents a hydrogen atom;

$R_5$ is at the 4-position of the phenyl and represents a bromine, chlorine or fluorine atom, or a methoxy;

$R_6$ represents a hydrogen atom;

$R_7$ represents a hydrogen atom;

$R_8$ is at the 4-position of the phenyl and represents a hydrogen atom, a chlorine atom, a fluorine atom;

$R_9$ is at the 2-position of the phenyl and represents a chlorine or fluorine atom;

in the form of a base or of an addition salt with an acid, and in the form of a hydrate or a solvate.

Among the compounds of formula (I) which are the subject of the invention, the following compounds may be mentioned in particular:

N-[[5-(4-bromophenyl)-1-(2,4-dichlorophenyl)-4-methyl-1H-pyrazol-3-yl]methyl]butane-1-sulfonamide;

N-[[5-(4-bromophenyl)-1-(2,4-dichlorophenyl)-4-methyl-1H-pyrazol-3-yl]methyl]-cyclohexanesulfonamide;

N-[[5-(4-bromophenyl)-1-(2,4-dichlorophenyl)-4-methyl-1H-pyrazol-3-yl]methyl]-cyclohexylmethanesulfonamide;

N-[[5-(4-bromophenyl)-1-(2,4-dichlorophenyl)-4-methyl-1H-pyrazol-3-yl]methyl]-3-chlorobenzenesulfonamide;

N-[[5-(4-bromophenyl)-1-(2,4-dichlorophenyl)-4-methyl-1H-pyrazol-3-yl]methyl]-4-tert-butylbenzenesulfonamide;

N-[[5-(4-bromophenyl)-1-(2,4-dichlorophenyl)-4-methyl-1H-pyrazol-3-yl]methyl]-3-methoxybenzenesulfonamide;

N-[[5-(4-bromophenyl)-1-(2,4-dichlorophenyl)-4-methyl-1H-pyrazol-3-yl]methyl]-4-methoxybenzenesulfonamide;

N-[[5-(4-bromophenyl)-1-(2,4-dichlorophenyl)-4-methyl-1H-pyrazol-3-yl]methyl]-4-(trifluoromethyl)benzenesulfonamide;

N-[[5-(4-bromophenyl)-1-(2,4-dichlorophenyl)-4-methyl-1H-pyrazol-3-yl]methyl]-2-(methylsulfonyl)benzenesulfonamide;

N-[[5-(4-bromophenyl)-1-(2,4-dichlorophenyl)-4-methyl-1H-pyrazol-3-yl]methyl]-1-(3-chlorophenyl)methanesulfonamide;

N-[[5-(4-bromophenyl)-1-(2,4-dichlorophenyl)-4-methyl-1H-pyrazol-3-yl]methyl]-1-[3-(trifluoromethyl)phenyl]methanesulfonamide;

N-[[5-(4-bromophenyl)-1-(2,4-dichlorophenyl)-4-methyl-1H-pyrazol-3-yl]methyl]-3-chloro-4-fluorobenzenesulfonamide;

N-[[5-(4-chlorophenyl)-1-(2,4-dichlorophenyl)-4-methyl-1H-pyrazol-3-yl]methyl]-butane-1-sulfonamide;

3-chloro-N-[[5-(4-chlorophenyl)-1-(2,4-dichlorophenyl)-4-methyl-1H-pyrazol-3-yl]methyl]benzenesulfonamide;

4-tert-butyl-N-[[5-(4-chlorophenyl)-1-(2,4-dichlorophenyl)-4-methyl-1H-pyrazol-3-yl]methyl]benzenesulfonamide;

N-[[5-(4-chlorophenyl)-1-(2,4-dichlorophenyl)-4-methyl-1H-pyrazol-3-yl]methyl]-3-methoxybenzenesulfonamide;

N-[[5-(4-chlorophenyl)-1-(2,4-dichlorophenyl)-4-methyl-1H-pyrazol-3-yl]methyl]-3-cyanobenzenesulfonamide;

N-[[5-(4-chlorophenyl)-1-(2,4-dichlorophenyl)-4-methyl-1H-pyrazol-3-yl]methyl]-4-(trifluoromethyl)benzenesulfonamide;

N-[[5-(4-chlorophenyl)-1-(2,4-dichlorophenyl)-4-methyl-1H-pyrazol-3-yl]methyl]-2-(trifluoromethoxy)benzenesulfonamide;

N-[[5-(4-chlorophenyl)-1-(2,4-dichlorophenyl)-4-methyl-1H-pyrazol-3-yl]methyl]-2-(methylsulfonyl)benzenesulfonamide;

3-chloro-N-[[5-(4-chlorophenyl)-1-(2,4-dichlorophenyl)-4-methyl-1H-pyrazol-3-yl]methyl]-4-fluorobenzenesulfonamide;

4-bromo-N-[[5-(4-chlorophenyl)-1-(2,4-dichlorophenyl)-4-methyl-1H-pyrazol-3-yl]methyl]-2-ethylbenzenesulfonamide;

N-[[5-(4-bromophenyl)-1-(2,4-dichlorophenyl)-4-ethyl-1H-pyrazol-3-yl]methyl]ethanesulfonamide;

N-[[5-(4-bromophenyl)-1-(2,4-dichlorophenyl)-4-ethyl-1H-pyrazol-3-yl]methyl]propane-2-sulfonamide;

N-[[5-(4-bromophenyl)-1-(2,4-dichlorophenyl)-4-ethyl-1H-pyrazol-3-yl]methyl]butane-1-sulfonamide;

N-[[5-(4-bromophenyl)-1-(2,4-dichlorophenyl)-4-ethyl-1H-pyrazol-3-yl]methyl]-cyclohexanesulfonamide;

N-[[5-(4-bromophenyl)-1-(2,4-dichlorophenyl)-4-ethyl-1H-pyrazol-3-yl]methyl]-1-cyclohexylmethanesulfonamide;
N-[[5-(4-bromophenyl)-1-(2,4-dichlorophenyl)-4-ethyl-1H-pyrazol-3-yl]methyl]-3-chlorobenzenesulfonamide;
N-[[5-(4-bromophenyl)-1-(2,4-dichlorophenyl)-4-ethyl-1H-pyrazol-3-yl]methyl]-2-chlorobenzenesulfonamide;
N-[[5-(4-bromophenyl)-1-(2,4-dichlorophenyl)-4-ethyl-1H-pyrazol-3-yl]methyl]-3-methylbenzenesulfonamide;
N-[[5-(4-bromophenyl)-1-(2,4-dichlorophenyl)-4-ethyl-1H-pyrazol-3-yl]methyl]-4-tert-butylbenzenesulfonamide;
N-[[5-(4-bromophenyl)-1-(2,4-dichlorophenyl)-4-ethyl-1H-pyrazol-3-yl]methyl]-4-methoxybenzenesulfonamide;
N-[[5-(4-bromophenyl)-1-(2,4-dichlorophenyl)-4-ethyl-1H-pyrazol-3-yl]methyl]-3-methoxybenzenesulfonamide;
N-[[5-(4-bromophenyl)-1-(2,4-dichlorophenyl)-4-ethyl-1H-pyrazol-3-yl]methyl]-4-(trifluoromethyl)benzenesulfonamide;
N-[[5-(4-bromophenyl)-1-(2,4-dichlorophenyl)-4-ethyl-1H-pyrazol-3-yl]methyl]-3-(trifluoromethyl)benzenesulfonamide;
N-[[5-(4-bromophenyl)-1-(2,4-dichlorophenyl)-4-ethyl-1H-pyrazol-3-yl]methyl]-2-(trifluoromethyl)benzenesulfonamide;
N-[[5-(4-bromophenyl)-1-(2,4-dichlorophenyl)-4-ethyl-1H-pyrazol-3-yl]methyl]-3-(trifluoromethoxy)benzenesulfonamide;
N-[[5-(4-bromophenyl)-1-(2,4-dichlorophenyl)-4-ethyl-1H-pyrazol-3-yl]methyl]-2-(trifluoromethoxy)benzenesulfonamide;
3-acetyl-N-[[5-(4-bromophenyl)-1-(2,4-dichlorophenyl)-4-ethyl-1H-pyrazol-3-yl]methyl]benzenesulfonamide;
N-[[5-(4-bromophenyl)-1-(2,4-dichlorophenyl)-4-ethyl-1H-pyrazol-3-yl]methyl]biphenyl-3-sulfonamide;
N-[[5-(4-bromophenyl)-1-(2,4-dichlorophenyl)-4-ethyl-1H-pyrazol-3-yl]methyl]-1-[4-(trifluoromethyl)phenyl]methanesulfonamide;
N-[[5-(4-bromophenyl)-1-(2,4-dichlorophenyl)-4-ethyl-1H-pyrazol-3-yl]methyl]-1-[3-(trifluoromethyl)phenyl]methanesulfonamide;
N-[[5-(4-bromophenyl)-1-(2,4-dichlorophenyl)-4-ethyl-1H-pyrazol-3-yl]methyl]-3,5-dimethylbenzenesulfonamide;
N-[[5-(4-bromophenyl)-1-(2,4-dichlorophenyl)-4-ethyl-1H-pyrazol-3-yl]methyl]-3,5-bis(trifluoromethyl)benzenesulfonamide;
3-chloro-N-[[1-(2-chlorophenyl)-5-(4-chlorophenyl)-4-methyl-1H-pyrazol-3-yl]methyl]benzenesulfonamide;
N-[[1-(2-chlorophenyl)-5-(4-chlorophenyl)-4-methyl-1H-pyrazol-3-yl]methyl]-2-fluorobenzenesulfonamide;
N-[[1-(2-chlorophenyl)-5-(4-chlorophenyl)-4-methyl-1H-pyrazol-3-yl]methyl]-3-cyanobenzenesulfonamide;
N-[[1-(2-chlorophenyl)-5-(4-chlorophenyl)-4-methyl-1H-pyrazol-3-yl]methyl]-3-methoxybenzenesulfonamide;
N-[[5-(4-bromophenyl)-1-(2,4-dichlorophenyl)-4-methyl-1H-pyrazol-3-yl]methyl]-3-methoxybenzenesulfonamide;
N-[[5-(4-bromophenyl)-1-(2,4-dichlorophenyl)-4-methyl-1H-pyrazol-3-yl]methyl]-3-cyanobenzenesulfonamide;
N-[[5-(4-bromophenyl)-1-(2,4-dichlorophenyl)-4-ethyl-1H-pyrazol-3-yl]methyl]-1-(2-fluorophenyl)methanesulfonamide;
N-[[5-(4-bromophenyl)-1-(2,4-dichlorophenyl)-4-ethyl-1H-pyrazol-3-yl]methyl]-1-(4-fluorophenyl)methanesulfonamide;
5-bromo-N-[[5-(4-bromophenyl)-1-(2,4-dichlorophenyl)-4-ethyl-1H-pyrazol-3-yl]methyl]thiophene-2-sulfonamide;
N-[[5-(4-bromophenyl)-1-(2,4-dichlorophenyl)-4-ethyl-1H-pyrazol-3-yl]methyl]-5-isoxazol-3-ylthiophene-2-sulfonamide;
3-chloro-N-[[1-(2,4-dichlorophenyl)-5-(4-methoxyphenyl)-4-methyl-1H-pyrazol-3-yl]methyl]benzenesulfonamide;
N-[[1-(2,4-dichlorophenyl)-5-(4-methoxyphenyl)-4-methyl-1H-pyrazol-3-yl]methyl]-3-methylbenzenesulfonamide;

in the form of a base or of an addition salt with an acid, and in the form of a hydrate or of a solvate.

In the text that follows, the expression protecting group Pg is understood to mean a group which makes it possible, on the one hand, to protect a reactive functional group such as a hydroxyl or an amine during synthesis and, on the other hand, to regenerate the intact reactive functional group at the end of the synthesis. Examples of protecting groups and methods of protection and deprotection are given in "Protective Group in Organic Synthesis", Green et al., $2^{nd}$ Edition (John Wiley & Sons, Inc., New York), 1991.

The expression leaving group is understood to mean, in the text which follows, a group which can be easily cleaved from a molecule by rupturing a heterolytic bond, with departure of an electron pair. This group can thus be easily replaced by another group during a substitution reaction, for example. Such leaving groups are, for example, halogens or an activated hydroxyl group such as a methanesulfonate, benzenesulfonate, p-toluenesulfonate, triflate, acetate and the like. Examples of leaving groups and references for their preparation are given in "Advances in Organic Chemistry", J. March, $3^{rd}$ Edition, Wiley Interscience, 1985, p. 310-316.

In accordance with the invention, the compound of formula (I) may be prepared according to a method which is characterized in that: a compound of formula:

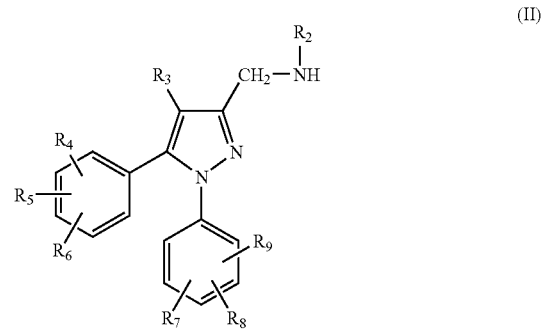

(II)

in which $R_2$, $R_3$, $R_4$, $R_5$, $R_6$, $R_7$, $R_8$ and $R_9$ are as defined for a compound of formula (I), is reacted, in the presence of a base and in a solvent, with a sulfonyl halide of formula:

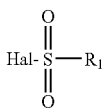

(III)

in which $R_1$ is as defined for a compound of formula (I) and Hal represents a halogen atom.

Optionally, the compound of formula (I) is converted to one of its addition salts with an acid.

The reaction is carried out in the presence of a base such as triethylamine or diisopropylethylamine, in a solvent such as dichloromethane or tetrahydrofuran, and at a temperature between room temperature and the reflux temperature of the solvent. The reaction is preferably carried out using a compound of formula (III) in which Hal represents a chlorine atom.

According to another variant of the method, it is possible to prepare the compound of formula (I) in which $R_2$ represents a ($C_1$-$C_3$)alkyl by reacting a compound of formula (I) in which $R_2$=H with a ($C_1$-$C_3$)alkyl halide, in the presence of a base such as sodium hydroxide, or potassium carbonate, in a solvent such as N,N-dimethylformamide and at a temperature between room temperature and the reflux temperature of the solvent.

The compounds of formula (I) thus obtained may be subsequently separated from the reaction medium and purified according to conventional methods, for example by crystallization or chromatography.

The compounds of formula (II) are prepared by reacting a compound of formula:

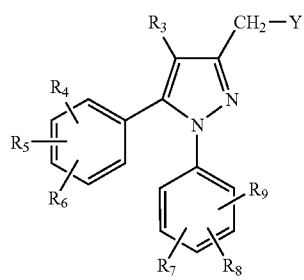

(IV)

in which $R_3$, $R_4$, $R_5$, $R_6$, $R_7$, $R_8$ and $R_9$ are as defined for a compound of formula (I) and Y represents a leaving group as defined above, preferably a halogen atom or an activated hydroxyl group such as a methanesulfonate, benzenesulfonate, p-toluenesulfonate or triflate group, with a compound of formula:

$H_2N-R_2$ (V)

in which $R_2$ is as defined for a compound of formula (I).

The reaction is carried out in a solvent such as N,N-dimethylformamide, acetonitrile, dichloromethane, toluene or propan-2-ol, and in the presence or in the absence of a base. When a base is used, it is chosen from organic bases such as triethylamine, N,N-diisopropylethylamine or N-methylmorpholine. The reaction is carried out at a temperature of between 0° C. and the reflux temperature of the solvent.

According to one variant, it is also possible to prepare a compound of formula (II) in which $R_2$=H by reacting a compound of formula (IV) in which Y=Cl with 1,3,5,7-tetraazatricyclo[3.3.1$^{3.7}$]decane (or hexamethylenetetramine) followed by hydrolysis with a strong acid such as hydrochloric acid.

The compounds of formula (III) are commercially available or are described in the literature, or may be prepared according to methods which are described therein, for example in J. Org. Chem. USSR, 1970, 6, 2454-2458; J. Am. Chem. Soc., 1952, 74, 2008; J. Med. Chem., 1977, 20(10), 1235-1239; EP 0 469 984; WO 95/18105.

For example, the compounds of formula (III) may be prepared by halogenation of the corresponding sulfonic acids or of their salts, for example of their sodium or potassium salts. The reaction is carried out in the presence of a halogenating agent such as phosphorus oxychloride, thionyl chloride, phosphorus trichloride, phosphorus tribromide or phosphorus pentachloride, with no solvent or in a solvent such as a halogenated hydrocarbon or N,N-dimethylformamide and at a temperature of between −10° C. and 200° C.

The compounds of formula (IV) are prepared from the compounds of formula:

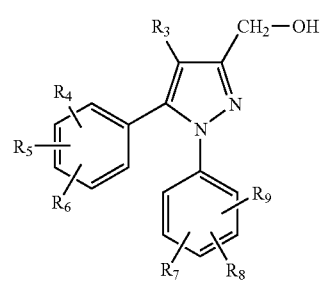

(VI)

in which $R_3$, $R_4$, $R_5$, $R_6$, $R_7$, $R_8$ and $R_9$ are as defined for a compound of formula (I), according to conventional methods cited above.

Thus, for example, when in a compound of formula (IV) Y represents a halogen atom, a compound of formula (VI) is treated with a halogenating agent such as $PCl_5$, $PBr_3$, HBr or $BBr_3$, in a solvent such as dichloromethane and at a temperature between 0° C. and room temperature.

When, in a compound of formula (IV), Y represents a methanesulfonate, a benzenesulfonate, a p-toluene-sulfonate or a trifluoromethanesulfonate, a compound of formula (VI) is reacted with a sulfonyl chloride of formula X—$SO_2$—Cl in which X represents a methyl, a phenyl, a p-tolyl or a trifluoromethyl. The reaction is carried out in the presence of a base such as triethylamine, pyridine or N,N-diisopropylethylamine, in a solvent such as dichloromethane or toluene and at a temperature between −20° C. and the reflux temperature of the solvent.

The compounds of formula (V) are known.

The compounds of formula (VI) are prepared by a reaction for reducing the compounds of formula:

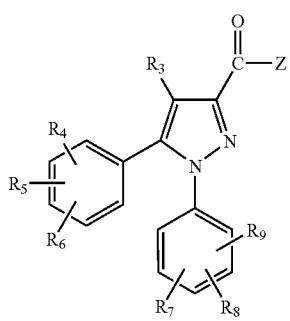

(VII)

in which $R_3$, $R_4$, $R_5$, $R_6$, $R_7$, $R_8$ and $R_9$ are as defined for a compound of formula (I) and Z represents a hydroxyl or a $(C_1-C_2)$alkoxy.

The reaction is carried out in the presence of a reducing agent such as sodium borohydride or lithium aluminum hydride, in a solvent such as tetrahydrofuran, and at a temperature between −20° C. and room temperature. When a compound of formula (VII) in which Z=OH is reduced, the acid may be activated beforehand by reaction with ethyl chloroformate in the presence of triethylamine.

The compounds of formula (VII) are known and are prepared according to known methods such as those described in EP 0656 354, EP 0576 357 or in WO 00/46209.

The following examples describe the preparation of certain compounds in accordance with the invention. These examples are not limiting and merely illustrate the present invention. The numbers for the compounds exemplified refer to those given in Table V below, which illustrates the chemical structures and the physical properties of a few compounds according to the invention.

In the preparations and in the examples, the following abbreviations are used:
ether: diethyl ether
iso-ether: diisopropyl ether
DMSO: dimethyl sulfoxide
DMF: N,N-dimethylformamide
THF: tetrahydrofuran
DCM: dichloromethane
AcOEt: ethyl acetate
DIPEA: diisopropylethylamine
TFA: trifluoroacetic acid
hydrochloric ether 2N: 2N solution of hydrochloric acid in diethyl ether
m.p.: melting point
RT: room temperature
b.p.: boiling point
HPLC: high performance liquid chromatography
silica H: silica 60 H gel marketed by Merck (DARMSTAD)
buffer solution pH=2: solution of 16.66 g of $KHSO_4$ and 32.32 g of $K_2SO_4$ in 1 liter of water.

The nuclear magnetic resonance spectra are recorded at 200 MHz in DMSO-$d_6$. For the interpretation of the spectra, the following abbreviations are used: s: singlet, d: doublet, t: triplet, m: unresolved complex, mt: multiplet, bs: broad s.

The compounds according to the invention are analyzed by LC/UV/MS (liquid chromatography/UV detection/mass spectrometry) coupling. The molecular peak (MH⁺) and the retention time (tr) in minutes are measured.

The apparatus used, marketed by Agilent, is composed of a chromatograph HP 1100 equipped with an Agilent diode array detector and an MSD Quad quadripole mass spectrometer.

Method A:

There is used an Xterra Waters® MS C18 column, marketed by Waters, 2.1×30 mm, 3.5 μm, at room temperature, flow rate 1 ml/minute.

The eluant is made up as follows:
solvent A: 0.025% trifluoroacetic acid (TFA) in water;
solvent B: 0.025% TFA in acetonitrile.

Gradient: the percentage of solvent B varies from 0 to 100% within 2 minutes with a plateau at 100% B for 1 minute.

The UV detection is carried out between 210 nm and 400 nm and the mass detection in chemical ionization mode at atmospheric pressure.

Method B:

There is used a Symmetry C18 column 2.1×50 mm, 3.5 μm, at 30° C., flow rate 0.4 ml/minute.

The eluant is made up as follows:
solvent A: 0.005% trifluoroacetic acid (TFA) in water at pH 3.15;
solvent B: 0.005% TFA in acetonitrile.

Gradient:

| Time (minute) | % A | % B |
|---|---|---|
| 0 | 100 | 0 |
| 10 | 10 | 90 |
| 15 | 10 | 90 |
| 16 | 100 | 0 |
| 20 | 100 | 0 |

The UV detection is carried out at λ=210 nM and the mass detection is carried out in positive electrospray mode (ESI).

Method C:

There is used a Symmetry C18 column 2.1×50 mm, 3.5 μm, at 30° C., flow rate 0.4 ml/minute.

The eluant is made up as follows:
solvent A: 0.005% TFA in water at pH 3.15;
solvent B: 0.005% TFA in acetonitrile.

Gradient:

| Time (minute) | % A | % B |
|---|---|---|
| 0 | 100 | 0 |
| 20 | 10 | 90 |
| 30 | 10 | 90 |
| 35 | 100 | 0 |
| 40 | 100 | 0 |

The UV detection is carried out at λ=210 nM and the mass detection is carried out in positive electrospray mode (ESI).

Method D:

There is used an Xterra MS C18 column 2.1×50 mm, 3.5 μm, at 30° C., flow rate 0.4 ml/minute.

The eluant is made up as follows:

solvent A: 10 nM ammonium acetate(AcONH$_4$) in water at pH 7;

solvent B: acetonitrile.

Gradient:

| Time (minute) | % A | % B |
|---|---|---|
| 0 | 100 | 0 |
| 10 | 10 | 90 |
| 15 | 10 | 90 |
| 16 | 100 | 0 |
| 20 | 100 | 0 |

The UV detection is carried out at λ=220 nM and the mass detection is carried out in positive electrospray mode (ESI).

Method E:

There is used an Xterra MS C18 column 2.1×50 mm, 3.5 μm, at 30° C., flow rate 0.4 ml/minute.

The eluant is made up as follows:

solvent A: 10 nM AcONH$_4$ in water at pH 7;

solvent B: acetonitrile.

Gradient:

| Time (minute) | % A | % B |
|---|---|---|
| 0 | 100 | 0 |
| 20 | 10 | 90 |
| 30 | 10 | 90 |
| 35 | 100 | 0 |
| 40 | 100 | 0 |

PREPARATIONS

1. Preparations of the Compounds of Formula (VII)

Preparation 1.1

5-(4-Bromophenyl)-1-(2,4-dichlorophenyl)-4-methyl-1H-pyrazole-3-carboxylic acid (VII): $R_3$=—CH$_3$; $R_4$=H; $R_5$=4-Br; $R_6$=H; $R_7$=H; $R_8$=4-Cl; $R_9$=2-Cl.; Z=—OH.

A) Lithium salt of ethyl 4-(4-bromophenyl)-3-methyl-2-oxo-4-oxydobut-3-enoate

A solution of 43 g of the lithium salt of hexamethyldisilazane in 300 ml of ether is cooled to −60° C., a solution of 50 g of 4-bromopropiophenone is added dropwise in 500 ml of ether and the mixture is kept stirring until the temperature rises to −30° C. 38 g of diethyl oxalate are then added and the mixture is kept stirring for 18 hours, the temperature being allowed to rise to RT. The precipitate formed is drained, it is washed with ether and it is dried under vacuum. 62 g of the expected product are obtained.

B) Ethyl 5-(4-bromophenyl)-1-(2,4-dichlorophenyl)-4-methyl-1H-pyrazole-3-carboxylate To a solution of 30 g of the compound obtained in the preceding step in 150 ml of acetic acid are added 20 g of 2,4-dichlorophenylhydrazine hydrochloride and the mixture is heated under reflux for 3 hours. After cooling to RT, the reaction mixture is poured into a water/ice mixture, extracted with ether, the organic phase is washed with a saturated NaCl solution, dried over MgSO$_4$, the solvent is partially evaporated under vacuum and the crystallized product formed is drained. 33.4 g of the expected product are obtained.

C) 5-(4-Bromophenyl)-1-(2,4-dichlorophenyl)-4-methyl-1H-pyrazole-3-carboxylic acid To a solution of 26 g of the compound obtained in the preceding step in 50 ml of EtOH are added 6.5 g of KOH and then 20 ml of water and the mixture is heated under reflux for 2 hours. After cooling to RT, the reaction mixture is poured into a water/ice mixture containing 10 ml of concentrated HCl, the precipitate formed is drained, washed with water and dried under vacuum. 24 g of the expected product are obtained.

Preparation 1.2

Methyl 5-(4-chlorophenyl)-1-(2,4-dichlorophenyl)-4-methyl-1H-pyrazole-3-carboxylate (VII): $R_3$=—CH$_3$; $R_4$=H; $R_5$=4-Cl; $R_6$=H; $R_7$=H; $R_8$=4-Cl; $R_9$=2-Cl; Z=—OCH$_3$.

A) 5-(4-Chlorophenyl)-1-(2,4-dichlorophenyl)-4-methyl-1H-pyrazole-3-carboxylic acid This compound is prepared according to the operating methods described in EP 0 656 354B.

B) Methyl 5-(4-chlorophenyl)-1-(2,4-dichlorophenyl)-4-methyl-1H-pyrazole-3-carboxylate To a solution of 30 g of the compound obtained in the preceding step in 500 ml of MeOH are added 3 g of para-toluenesulfonic acid and the mixture is heated under reflux for 2 hours. The reaction mixture is concentrated under vacuum by half, the precipitate formed is drained, washed with MeOH and dried. 30 g of the expected product are obtained.

Preparation 1.3

5-(4-Bromophenyl)-1-(2,4-dichlorophenyl)-4-ethyl-1H-pyrazole-3-carboxylic acid (VII): $R_3$=—CH$_2$CH$_3$; $R_4$=H; $R_5$=4-Br; $R_6$=H; $R_7$=H; $R_8$=4-Cl; $R_9$=2-Cl; Z=—OH.

This compound is prepared according to the procedures described in WO 00/46209.

By following the procedures described in Preparations 1 above, the compounds of formula (VII) assembled in TABLE I below are prepared.

TABLE I

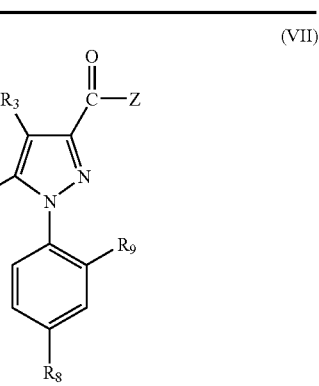

(VII)

| Preparations | R$_3$ | R$_5$ | R$_8$ | R$_9$ | Z |
|---|---|---|---|---|---|
| 1.1 | —CH$_3$ | Br | Cl | Cl | —OH |
| 1.2 | —CH$_3$ | Cl | Cl | Cl | —OCH$_3$ |
| 1.3 | —CH$_2$CH$_3$ | Br | Cl | Cl | —OH |
| 1.4 | —CH$_3$ | Cl | H | Cl | —OCH$_2$OCH$_3$ |
| 1.5 | —CH$_3$ | F | H | Cl | —OCH$_2$OCH$_3$ |
| 1.6 | —CH$_3$ | —OCH$_3$ | H | Cl | —OCH$_2$OCH$_3$ |
| 1.7 | —CH$_3$ | —OCH$_3$ | H | F | —OCH$_2$OCH$_3$ |
| 1.8 | —CH$_3$ | —OCH$_3$ | Cl | Cl | —OCH$_2$OCH$_3$ |
| 1.9 | —CH$_3$ | —OCH$_3$ | F | F | —OCH$_2$OCH$_3$ |

R$_4$ = H;
R$_6$ = H;
R$_7$ = H;

2. Preparations of the Compounds of Formula (VI).
Preparation 2.1

[5-(4-Bromophenyl)-1-(2,4-dichlorophenyl)-4-methyl-1H-pyrazol-3-yl]methanol (VI): R$_3$=—CH$_3$; R$_4$=H; R$_5$=4-Br; R$_6$=H; R$_7$=H; R$_8$=4-Cl; R$_9$=2-Cl.

A mixture of 24 g of the compound obtained in Preparation 1.1 in 200 ml of THF is cooled to −10° C., 7.8 ml of triethylamine are added, followed dropwise by 5.38 ml of ethyl chloroformate and the mixture is kept stirring for 15 minutes at −10° C. 6.3 g of sodium borohydride are then added all at once and at a temperature of less than −10° C., followed dropwise by 100 l of MeOH and the mixture is kept stirring for 30 minutes at 0° C. The reaction mixture is hydrolyzed by adding 100 ml of 10% HCl, it is concentrated under vacuum, the residue is taken up in water, extracted with AcOEt, the organic phase is washed with a saturated NaCl solution, dried over MgSO$_4$ and the solvent is evaporated under vacuum. The residue is chromatographed on silica gel, eluting with the cyclohexane/AcOEt mixture (75/25; v/v). 22 g of the expected product are obtained.

Preparation 2.2

[5-(4-Chlorophenyl)-1(2,4-dichlorophenyl)-4-methyl-1H-pyrazol-3-yl]methanol (VI): R$_3$=—CH$_3$; R$_4$=H; R$_5$=4-Cl; R$_6$=H; R$_7$=H; R$_8$=4-Cl; R$_9$=2-Cl.

A solution of 30 g of the compound obtained in Preparation 1.2 in 500 ml of THF is cooled to −5° C., 4.6 g of lithium aluminum hydride are added in small portions and while maintaining the temperature between −5° C. and 0° C. and the mixture is kept stirring for 1 hour at RT. The reaction mixture is cooled to 0° C., hydrolyzed by adding 20 ml of 1N NaOH, the inorganics are filtered, washed with THF and the filtrate is concentrated under vacuum. The residue is extracted with ether, the organic phase is washed with a saturated NaCl solution, dried over Na$_2$SO$_4$ and the solvent is partially evaporated under vacuum. The precipitate formed is drained, washed with ether and dried. 25 g of the expected product are obtained.

Preparation 2.3

[5-(4-Bromophenyl)-1-(2,4-dichlorophenyl)-4-ethyl-1H-pyrazol-3-yl]methanol (VI): R$_3$=—CH$_2$CH$_3$; R$_4$=H; R$_5$=4-Br; R$_6$=H; R$_7$=H; R$_8$=4-Cl; R$_9$=2-Cl.

A mixture of 24.6 g of the compound obtained in Preparation 1.3 in 200 ml of THF is cooled to −10° C., 7.8 ml of triethylamine are added, followed dropwise by 5.38 ml of ethyl chloroformate and the mixture is kept stirring for 15 minutes at −10° C. 6.3 g of sodium borohydride are then added all at once and at a temperature of less than −10° C., followed dropwise by 100 ml of MeOH. The reaction mixture is hydrolyzed at 0° C. by adding 100 ml of 10% HCl and then concentrated under vacuum. The residue is extracted with AcOEt, the organic phase is washed twice with 50 ml of a saturated NaCl solution, dried over Na$_2$SO$_4$ and the solvent is evaporated under vacuum. The residue is chromatographed on silica gel, eluting with the cyclohexane/AcOEt mixture (60/40; v/v). 20 g of the expected product are obtained.

By following the procedures described in Preparations 2 above, the compounds of formula (VI) assembled in TABLE II below are prepared.

TABLE II (VI)

| Preparations | R$_3$ | R$_5$ | R$_8$ | R$_9$ |
|---|---|---|---|---|
| 2.1 | —CH$_3$ | Br | Cl | Cl |
| 2.2 | —CH$_3$ | Cl | Cl | Cl |
| 2.3 | —CH$_2$CH$_3$ | Br | Cl | Cl |
| 2.4 | —CH$_3$ | Cl | H | Cl |
| 2.5 | —CH$_3$ | F | H | Cl |
| 2.6 | —CH$_3$ | —OCH$_3$ | H | Cl |
| 2.7 | —CH$_3$ | —OCH$_3$ | H | F |
| 2.8 | —CH$_3$ | —OCH$_3$ | Cl | Cl |
| 2.9 | —CH$_3$ | —OCH$_3$ | F | F |

R$_4$ = H;
R$_6$ = H;
R$_7$ = H;

3. Preparations of the Compounds of Formula (IV)

Preparation 3.1

5-(4-Bromophenyl)-3-(chlorophenyl)-1-(2,4-dichlorophenyl)-4-methyl-1H-pyrazole (IV): $R_3$=—$CH_3$; $R_4$=H; $R_5$=4-Br; $R_6$=H; $R_7$=H; $R_8$=4-Cl; $R_9$=2-Cl; Y=Cl.

A solution of 20 g of the compound obtained in Preparation 2.1 in 250 ml of DCM is cooled to 0° C. under a nitrogen atmosphere, 10.6 g of phosphorus pentachloride are added in small fractions and at a temperature of less than 5° C. and the mixture is kept stirring for 2 hours, the temperature being allowed to rise to RT. The reaction mixture is poured into 150 ml of a water/ice mixture and the mixture is kept stirring for 10 minutes. The mixture is extracted with DCM, the organic phase is washed with a 5% $NaHCO_3$ solution, with a saturated NaCl solution, dried over $MgSO_4$ and the solvent is evaporated under vacuum. 24 g of the expected product are obtained.

Preparation 3.2

3-(Chloromethyl)-5-(4-chlorophenyl)-1-(2,4-dichlorophenyl)-4-methyl-1H-pyrazole (IV): $R_3$=—$CH_3$; $R_4$=H; $R_5$=4-Cl; $R_6$=H; $R_7$=H; $R_8$=4-Cl; $R_9$=2-Cl; Y=Cl.

A solution of 25 g of the compound obtained in Preparation 2.2 in 250 ml of DCM is cooled to 0° C. under a nitrogen atmosphere, 14.8 g of phosphorus pentachloride are added in small fractions and at a temperature of between 0° C. and 5° C. and the mixture is kept stirring for 3 hours, the temperature being allowed to rise to RT. The reaction mixture is poured into 200 ml of water and kept stirring for 10 minutes. After decantation, the organic phase is washed with a saturated $NaHCO_3$ solution, with a saturated NaCl solution, dried over $Na_2SO_4$ and the solvent is evaporated under vacuum. 25 g of the expected product are obtained in the form of a meringue.

Preparation 3.3

5-(4-Bromophenyl)-3-(chloromethyl)-1-(2,4-dichlorophenyl)-4-ethyl-1H-pyrazole (IV): $R_3$=—$CH_2CH_3$; $R_4$=H; $R_5$=4-Br; $R_6$=H; $R_7$=H; $R_8$=4-Cl; $R_9$=2-Cl; Y=Cl This compound is prepared according to the procedure described in Preparation 3.2 from 9 g of the compound obtained in Preparation 2.3 in 200 ml of DCM and 4.6 g of phosphorus pentachloride. 9.4 g of the expected product are obtained.

By carrying out the procedures as described in Preparations 3 above, the compounds of formula (IV) assembled in TABLE III below are prepared.

TABLE III (IV)

| Preparations | $R_3$ | $R_5$ | $R_8$ | $R_9$ | Y |
|---|---|---|---|---|---|
| 3.1 | —$CH_3$ | Br | Cl | Cl | Cl |
| 3.2 | —$CH_3$ | Cl | Cl | Cl | Cl |
| 3.3 | —$CH_2CH_3$ | Br | Cl | Cl | Cl |
| 3.4 | —$CH_3$ | Cl | H | Cl | Cl |
| 3.5 | —$CH_3$ | F | H | Cl | Cl |
| 3.6 | —$CH_3$ | —$OCH_3$ | H | Cl | Cl |
| 3.7 | —$CH_3$ | —$OCH_3$ | H | F | Cl |
| 3.8 | —$CH_3$ | —$OCH_3$ | Cl | Cl | Cl |
| 3.9 | —$CH_3$ | —$OCH_3$ | F | F | Cl |

$R_4$ = H;
$R_6$ = H;
$R_7$ = H;

4. Preparations of the Compounds of Formula (II)

Preparation 4.1

[[5-(4-Bromophenyl)-1-(2,4-dichlorophenyl)-4-methyl-1H-pyrazol-3-yl]methyl]amine hydrochloride (II), HCl: $R_2$=H; $R_3$=—$CH_3$; $R_4$=H; $R_5$=4-Br; $R_6$=H; $R_7$=H; $R_8$=4-Cl; $R_9$=2-Cl.

To a solution of 20 g of the compound obtained in Preparation 3.1 in 200 ml of chloroform are added 7 g of hexamethylenetetramine and the mixture is kept stirring for 5 days at RT. 50 ml of ether are then added, the precipitate formed is drained and dried. The precipitate is taken up in 50 ml of EtOH, 15 ml of concentrated HCl are added and the mixture is heated at 50° C. for 5 hours. The white insoluble matter is filtered and the filtrate is concentrated under vacuum. The residue is taken up in ether, the organic phase is washed with 50 ml of 5N NaOH, dried over $Na_2SO_4$ and the solvent is evaporated under vacuum. The residue is taken up in a 2N hydrochloric ether solution, the precipitate formed is drained, washed with ether and dried. 14.37 g of the expected product are obtained.

Preparation 4.2

[[5-(4-Chlorophenyl)-1-(2,4-dichlorophenyl)-4-methyl-1H-pyrazol-3-yl]methyl]amine hydrochloride (II), HCl: $R_2$=H; $R_3$=—$CH_3$; $R_4$=H; $R_5$=4-Cl; $R_6$=H; $R_7$=H; $R_8$=4-Cl; $R_9$=2-Cl.

This compound is prepared according to the procedure described in Preparation 4.1 from 25 g of the compound obtained in Preparation 3.2 in 150 ml of chloroform, 9 g of hexamethylenetetramine, 100 ml of ether, 250 ml of EtOH and 30 ml of concentrated HCl. 24 g of the expected product are obtained.

Preparation 4.3

[[5-(4-Bromophenyl)-1-(2,4-dichlorophenyl)-4-ethyl-1H-pyrazol-3-yl]methyl]amine hydrochloride (II), HCl: $R_2$=H; $R_3$=—$CH_2CH_3$; $R_4$=H; $R_5$=4-Br; $R_6$=H; $R_7$=H; $R_8$=4-Cl; $R_9$=2-Cl.

To a solution of 9 g of the compound obtained in Preparation 3.3 in 100 ml of chloroform are added 2.9 g of hexamethylenetetramine and the mixture is kept stirring for 10 days at RT. 50 ml of ether are then added, the mixture is kept stirring for 10 minutes, the reaction mixture is concentrated by half under vacuum, 50 ml of ether are added and the precipitate formed is drained. The precipitate is taken up in 50 ml of EtOH, 15 ml of concentrated HCl are added and the mixture is heated under reflux for 2 hours. The white insoluble matter is filtered and the filtrate is concentrated under vacuum. The residue is extracted with ether, the organic phase is washed with 20 ml of 1N NaOH, with a saturated NaCl solution, dried over $Na_2SO_4$ and the solvent is evaporated under vacuum. The residue is taken up in a 2N hydrochloric ether solution and the precipitate formed is drained. 8.5 g of the expected product are obtained.

By following the procedures described in Preparations 4 above, the compounds of formula (II) assembled in TABLE IV below are prepared.

TABLE IV (II)

| Preparations | $R_2$ | $R_3$ | $R_5$ | $R_8$ | $R_9$ |
|---|---|---|---|---|---|
| 4.1 | H | —$CH_3$ | Br | Cl | Cl |
| 4.2 | H | —$CH_3$ | Cl | Cl | Cl |
| 4.3 | H | —$CH_2CH_3$ | Br | Cl | Cl |
| 4.4 | H | —$CH_3$ | Cl | H | Cl |
| 4.5 | H | —$CH_3$ | F | H | Cl |
| 4.6 | H | —$CH_3$ | —$OCH_3$ | H | Cl |
| 4.7 | H | —$CH_3$ | —$OCH_3$ | H | F |
| 4.8 | H | —$CH_3$ | —$OCH_3$ | Cl | Cl |
| 4.9 | H | —$CH_3$ | —$OCH_3$ | F | F |

HCl: $R_4$ = H;
$R_6$ = H;
$R_7$ = H;

5. Preparations of the Compounds of Formula (III) Cyclohexanesulfonyl Chloride (III): $R_1$ = ⬡ ; Hal = Cl.

A mixture of 25 g of cyclohexanethiol in 83 ml of acetic acid and 4 ml of water is cooled to 0° C., and then chlorine gas is bubbled through until the yellow color persists. The reaction mixture is poured into water, extracted three times with ether, the combined organic phases are washed twice with water, dried over $Na_2SO_4$ and the solvent is evaporated under vacuum. The residue is distilled at a pressure of 4 Pa and 13.3 g of the expected product are obtained, b.p.=154° C.

EXAMPLE 1

Compound No. 8

N-[[5-(4-Bromophenyl)-1-(2,4-dichlorophenyl)-4-methyl-1H-pyrazol-3-yl]methyl]-4-(trifluoromethyl)benzene-sulfonamide

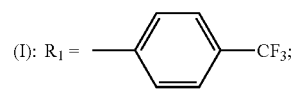

(I): $R_1$ = —⌬—$CF_3$;

$R_2$=H; $R_3$=—$CH_3$; $R_4$=H; $R_5$=4-Br; $R_6$=H; $R_7$=H; $R_8$=4-Cl; $R_9$=2-Cl

To a solution of 0.7 g of the compound obtained in Preparation 4.1 in 20 ml of DCM is added 0.42 ml of triethylamine, followed dropwise by 0.39 g of 4-(trifluoromethyl)benzenesulfonyl chloride and the mixture is kept stirring overnight at RT. 10 ml of water are added and the mixture is kept stirring for 10 minutes. After decantation, the organic phase is washed twice with a saturated $NaHCO_3$ solution, twice with a buffer solution pH=2, twice with a saturated NaCl solution, dried over $Na_2SO_4$ and the solvent is evaporated under vacuum. The product obtained is crystallized from a cyclohexane/AcOEt mixture (95/5; v/v). 0.75 g of the expected product is obtained, m.p.=195° C.

$^1$H NMR: DMSO-$d_6$: δ (ppm): 1.95: s: 3H, 4.15: S: 2H, 7.0: d: 2H, 7.2-8.1: m: 9H, 8.5: s: 1H.

EXAMPLE 2

Compound No. 28

N-[[5-(4-Bromophenyl)-1-(2,4-dichlorophenyl)-4-ethyl-1H-pyrazol-3-yl]methyl]-3-chlorobenzene-sulfonamide

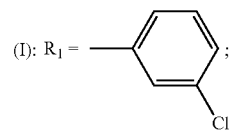

(I): $R_1$ = —⌬—Cl ;

$R_2$=H; $R_3$=—$CH_2CH_3$; $R_4$=H; $R_5$=4-Br; $R_6$=H; $R_7$=H; $R_8$=4-Cl; $R_9$=2-Cl

To a solution of 0.7 g of the compound obtained in Preparation 4.3 in 30 ml of DCM are added 0.4 ml of triethylamine, followed dropwise by 0.32 g of 3-chlorobenzenesulfonyl chloride and the mixture is kept stirring overnight at RT. The reaction mixture is concentrated under vacuum, the residue is extracted with AcOEt, the organic phase is washed twice with a saturated $NaHCO_3$ solution, twice with a buffer solution pH=2, twice with a saturated NaCl solution, dried over $Na_2SO_4$ and the solvent is evaporated under vacuum. The residue is chromatographed on silica gel, eluting with the cyclohexane/AcOEt mixture from (90/10; v/v) to (75/25; v/v). The product obtained is taken up in 1.5 ml of AcOEt, cyclohexane is added, the precipitate formed is drained and dried. 0.31 g of the expected product is obtained, m.p.=169° C.

$^1$H NMR: DMSO-$d_6$: δ (ppm): 1.0: t: 3H, 2.4: q: 2H, 4.15: s: 2H, 7.0: d: 2H, 7.2-7.9: m: 9H, 8.4: s: 1H.

EXAMPLE 3

Compound No. 42

N-[[5-(4-Bromophenyl)-1-(2,4-dichlorophenyl)-4-ethyl-1H-pyrazol-3-yl]methyl]-1-[3-(trifluoromethyl)phenyl]-methanesulfonamide

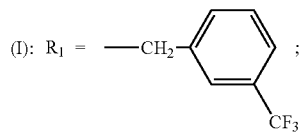

$R_2$=H; $R_3$=—$CH_2CH_3$; $R_4$=H; $R_5$=4-Br; $R_6$=H; $R_7$=H; $R_8$=4-Cl; $R_9$=2-Cl

To a solution of 0.5 g of the compound obtained in Preparation 4.3 in 25 ml of DCM is added 0.3 ml of triethylamine, followed by 0.28 g of [3-(trifluoromethyl)phenyl]methanesulfonyl chloride and the mixture is kept stirring overnight at RT. The reaction mixture is concentrated under vacuum, the residue is taken up in water, extracted with AcOEt, the organic phase is washed with a saturated $NaHCO_3$ solution, with a buffer solution pH=2, with a saturated NaCl solution, dried over $Na_2SO_4$ and the solvent is evaporated under vacuum. The residue is chromatographed on silica gel, eluting with the cyclohexane/AcOEt mixture from (90/10; v/v) to (85/15; v/v). 0.3 g of the expected compound is obtained, m.p.=108° C.

$^1$H NMR: DMSO-$d_6$: δ (ppm): 1.03: t: 3H, 2.5: mt: 2H; 4.23: d: 2H, 4.5: s: 2H, 7.13: d: 2H, 7.4-7.75: m: 9H; 7.80: t: 1H.

EXAMPLE 4

Compound No. 73

N-[[5-(4-Bromophenyl)-1-(2,4-dichlorophenyl)-4-ethyl-1H-pyrazol-3-yl]methyl]-3-chloro-N-methyl-benzene-sulfonamide

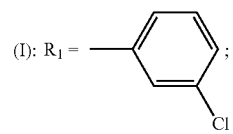

$R_2$=$CH_3$; $R_3$=—$CH_2CH_3$; $R_4$=H; $R_5$=4-Br; $R_6$=H; $R_7$=H; $R_8$=4-Cl; $R_9$=2-Cl

To a mixture of 0.41 g of compound No. 28 and 0.1 g of $K_2CO_3$ in 34 ml of DMF is added 0.05 ml of methyl iodide, followed by heating under reflux for 2 hours and the mixture is kept stirring overnight at RT. The reaction mixture is concentrated under vacuum, the residue is taken up in water, extracted with DCM, the organic phase is washed with a buffer solution of pH=2, with a saturated $NaHCO_3$ solution, with a saturated NaCl solution, dried over $Na_2SO_4$ and the solvent is evaporated under vacuum. The residue is chromatographed on silica gel, eluting with the cyclohexane/AcOEt mixture from (90/10; v/v) to (80/20; v/v). 0.263 g of the expected compound is obtained after drying under vacuum, m.p.=78° C.

The table which follows illustrates the chemical structures and the physical properties of some examples of compounds according to the invention. In this table:

- in the "salt" column "–" represents a compound in the form of a free base, while "HCl" represents a compound in hydrochloride form;
- in the column "method" represents one of the analytical methods used to determine the molecular peak MH$^+$ and the retention time as described above.

TABLE 1

(I)

| Compounds No. | $R_1$ | $R_2$ | $R_3$ | $R_5$ | $R_8$ | $R_9$ | Salt; m.p. ° C.; $MH^+$; tr (method) |
|---|---|---|---|---|---|---|---|
| 1 (a) | —CH$_2$CH$_2$CH$_2$CH$_3$ | H | —CH$_3$ | Br | Cl | Cl | —<br>—<br>530.36; 2.33<br>(method A) |
| 2 (a) | cyclohexyl | H | —CH$_3$ | Br | Cl | Cl | —<br>98;<br>— |
| 3 (a) | —CH$_2$-cyclohexyl | H | —CH$_3$ | Br | Cl | Cl | —<br>145;<br>— |
| 4 | 3-chlorophenyl | H | —CH$_3$ | Br | Cl | Cl | —<br>—<br>584.32; 2.41<br>(method A) |
| 5 (a) | 4-tert-butylphenyl | H | —CH$_3$ | Br | Cl | Cl | —<br>—<br>606.05; 2.31<br>(method A) |
| 6 (a) | 3-methoxyphenyl | H | —CH$_3$ | Br | Cl | Cl | —<br>—<br>579.97; 2,21<br>(method A) |
| 7 (a) | 4-methoxyphenyl | H | —CH$_3$ | Br | Cl | Cl | —<br>95;<br>— |
| 8 | 4-trifluoromethylphenyl | H | —CH$_3$ | Br | Cl | Cl | —<br>195;<br>— |
| 9 (a) | 2-(methylsulfonyl)phenyl | H | —CH$_3$ | Br | Cl | Cl | —<br>—<br>672.93;2.21<br>(method A) |

TABLE 1-continued (I)

| Compounds No. | R₁ | R₂ | R₃ | R₅ | R₈ | R₉ | Salt; m.p. °C.; MH⁺; tr (method) |
|---|---|---|---|---|---|---|---|
| 10 (a) | —CH₂—(3-Cl-phenyl) | H | —CH₃ | Br | Cl | Cl | —<br>95;<br>— |
| 11 (a) | —CH₂—(3-CF₃-phenyl) | H | —CH₃ | Br | Cl | Cl | —<br>96;<br>— |
| 12 (a) | 3-Cl-4-F-phenyl | H | —CH₃ | Br | Cl | Cl | —<br>—<br>602.29; 2.43 (method A) |
| 13 (b) | —CH₂CH₂CH₂CH₃ | H | —CH₃ | Cl | Cl | Cl | —<br>—<br>486.42; 2.30 (method A) |
| 14 (a) | 3-Cl-phenyl | H | —CH₃ | Cl | Cl | Cl | —<br>—<br>540.36; 2.39 (method A) |
| 15 (b) | 4-tert-butyl-phenyl | H | —CH₃ | Cl | Cl | Cl | —<br>115;<br>— |
| 16 (b) | 3-OCH₃-phenyl | H | —CH₃ | Cl | Cl | Cl | —<br>—<br>536.06; 2.20 (method A) |
| 17 (b) | 3-CN-phenyl | H | —CH₃ | Cl | Cl | Cl | —<br>—<br>531.02; 2.16 (method A) |

TABLE 1-continued

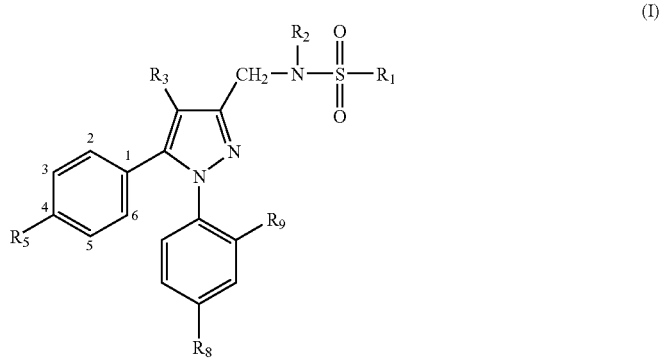

(I)

| Compounds No. | R₁ | R₂ | R₃ | R₅ | R₈ | R₉ | Salt; m.p. °C.; MH⁺; tr (method) |
|---|---|---|---|---|---|---|---|
| 18 (b) | 4-CF₃-phenyl | H | —CH₃ | Cl | Cl | Cl | — 189; — |
| 19 (b) | 2-OCF₃-phenyl | H | —CH₃ | Cl | Cl | Cl | — — 590.01; 2,25 (method A) |
| 20 (b) | 2-SO₂CH₃-phenyl | H | —CH₃ | Cl | Cl | Cl | Cl |
| 21 (b) | 4-F,3-Cl-phenyl | H | —CH₃ | Cl | Cl | Cl | — — 558.4; 2.41 (method A) |
| 22 (b) | 4-Br,3-CH₂CH₃-phenyl | H | —CH₃ | Cl | Cl | Cl | — — 611.96; 2.33 (method A) |
| 23 (c) | —CH₂CH₃ | H | —CH₂CH₃ | Br | Cl | Cl | — 125; — |
| 24 (c) | —CH(CH₃)₂ | H | —CH₂CH₃ | Br | Cl | Cl | — 157; — |
| 25 | —CH₂CH₂CH₂CH₃ | H | —CH₂CH₃ | Br | Cl | Cl | — 65; — |
| 26 (c) | cyclohexyl | H | —CH₂CH₃ | Br | Cl | Cl | — 98; — |
| 27 (c) | —CH₂-cyclohexyl | H | —CH₂CH₃ | Br | Cl | Cl | — 72; — |

TABLE 1-continued (I)

| Compounds No. | R₁ | R₂ | R₃ | R₅ | R₈ | R₉ | Salt; m.p. °C.; MH⁺; tr (method) |
|---|---|---|---|---|---|---|---|
| 28 (c) | 3-chlorophenyl | H | —CH₂CH₃ | Br | Cl | Cl | —<br>169;<br>— |
| 29 (c) | 2-chlorophenyl | H | —CH₂CH₃ | Br | Cl | Cl | —<br>135;<br>— |
| 30 (c) | 3-methylphenyl | H | —CH₂CH₃ | Br | Cl | Cl | —<br>165;<br>— |
| 31 (c) | 4-tert-butylphenyl | H | —CH₂CH₃ | Br | Cl | Cl | —<br>82;<br>— |
| 32 (c) | 4-methoxyphenyl | H | —CH₂CH₃ | Br | Cl | Cl | —<br>121;<br>— |
| 33 (c) | 3-methoxyphenyl | H | —CH₂CH₃ | Br | Cl | Cl | —<br>131;<br>— |
| 34 (c) | 4-trifluoromethylphenyl | H | —CH₂CH₃ | Br | Cl | Cl | —<br>65;<br>— |
| 35 (c) | 3-trifluoromethylphenyl | H | —CH₂CH₃ | Br | Cl | Cl | —<br>95;<br>— |

TABLE 1-continued (I)

| Compounds No. | R₁ | R₂ | R₃ | R₅ | R₈ | R₉ | Salt; m.p. ° C.; MH⁺; tr (method) |
|---|---|---|---|---|---|---|---|
| 36 (c) | 2-CF₃-phenyl | H | —CH₂CH₃ | Br | Cl | Cl | —<br>168;<br>— |
| 37 (c) | 3-OCF₃-phenyl | H | —CH₂CH₃ | Br | Cl | Cl | —<br>75;<br>— |
| 38 (c) | 2-OCF₃-phenyl | H | —CH₂CH₃ | Br | Cl | Cl | —<br>145;<br>— |
| 39 (c) | 3-COCH₃-phenyl | H | —CH₂CH₃ | Br | Cl | Cl | —<br>88;<br>— |
| 40 (c) | 3-biphenyl | H | —CH₂CH₃ | Br | Cl | Cl | —<br>183;<br>— |
| 41 (c) | —CH₂-(4-CF₃-phenyl) | H | —CH₂CH₃ | Br | Cl | Cl | —<br>87;<br>— |
| 42 (c) | —CH₂-(3-CF₃-phenyl) | H | —CH₂CH₃ | Br | Cl | Cl | —<br>108;<br>— |

TABLE 1-continued
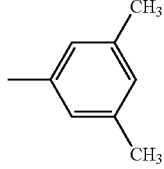
(I)
| Compounds No. | R₁ | R₂ | R₃ | R₅ | R₈ | R₉ | Salt; m.p. ° C.; MH⁺; tr (method) |
|---|---|---|---|---|---|---|---|
| 43 (c) | 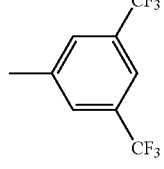 | H | —CH₂CH₃ | Br | Cl | Cl | — 153; — |
| 44 (c) | 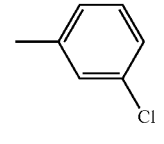 | H | —CH₂CH₃ | Br | Cl | Cl | — 105; — |
| 45 (d) | 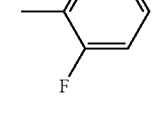 | H | —CH₃ | Cl | H | Cl | — — 506; 10.9 (method B) |
| 46 (d) | 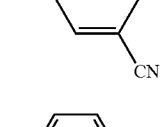 | H | —CH₃ | Cl | H | Cl | — — 490; 10.4 (method B) |
| 47 (d) | 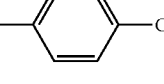 | H | —CH₃ | Cl | H | Cl | — — 497; 10.2 (method B) |
| 48 (d) | 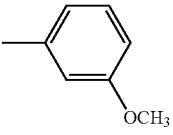 | H | —CH₃ | Cl | H | Cl | — 172; 497; 10.19 (method B) |
| 49 (d) |  | H | —CH₃ | Cl | H | Cl | — 151; 502; 10.5 (method B) |

TABLE 1-continued (I)

| Compounds No. | R₁ | R₂ | R₃ | R₅ | R₈ | R₉ | Salt; m.p. ° C.; MH⁺; tr (method) |
|---|---|---|---|---|---|---|---|
| 50 (d) | 3-(SO₂CH₃)-phenyl | H | —CH₃ | Cl | H | Cl | — 110; 550; 9.77 (method B) |
| 51 (d) | —CH₂-(3-CF₃-phenyl) | H | —CH₃ | Cl | H | Cl | — — 554; 11.1 (method B) |
| 52 (e) | 3-Cl-phenyl | H | —CH₃ | F | H | Cl | — 70; 490; 10.4 (method B) |
| 53 (e) | 2-F-phenyl | H | —CH₃ | F | H | Cl | — 147; 474; 9.9 (method B) |
| 54 (e) | 3-CN-phenyl | H | —CH₃ | F | H | Cl | — 80; 481; 9.7 (method B) |
| 55 (e) | —CH₂-(3-CF₃-phenyl) | H | —CH₃ | F | H | Cl | — 66; 538; 10.6 (method B) |
| 56 (f) | 3-Cl-phenyl | H | —CH₃ | —OCH₃ | H | Cl | — 73; 502; 10.1 (method B) |
| 57 (f) | 3-CH₃-phenyl | H | —CH₃ | —OCH₃ | H | Cl | — 66; 482; 10 (method B) |

TABLE 1-continued (I)

| Compounds No. | $R_1$ | $R_2$ | $R_3$ | $R_5$ | $R_8$ | $R_9$ | Salt; m.p. ° C.; $MH^+$; tr (method) |
|---|---|---|---|---|---|---|---|
| 58 (f) | 3-methoxyphenyl | H | —$CH_3$ | —$OCH_3$ | H | Cl | —; 65; 498; 9.7 (method B) |
| 59 (f) | 3-acetylphenyl | H | —$CH_3$ | —$OCH_3$ | H | Cl | —; 89; 510; 9.3 (method B) |
| 60 (f) | —$CH_2$-(2-fluorophenyl) | H | —$CH_3$ | —$OCH_3$ | H | Cl | —; 64; 500; 9.8 (method B) |
| 61 (f) | —$CH_2$-(3-trifluoromethylphenyl) | H | —$CH_3$ | —$OCH_3$ | H | Cl | —; 61; 550; 10.3 (method B) |
| 62 (f) | 2-biphenyl | H | —$CH_3$ | —$OCH_3$ | H | Cl | —; 140; 544; 10.6 (method D) |
| 63 (g) | 3-chlorophenyl | H | —$CH_3$ | —$OCH_3$ | H | F | —; —; 486; 9.9 (method B) |
| 64 (g) | 2-fluorophenyl | H | —$CH_3$ | —$OCH_3$ | H | F | —; 225; 470; 9.4 (method B) |

TABLE 1-continued (I)

[Structure: pyrazole with R3 at 4-position, CH2-N(R2)-S(=O)2-R1 at 3-position, phenyl ring at 5-position with positions 2,3,4,5,6 and R5 at position 4; N1-phenyl with R9 (ortho) and R8 (para)]

| Compounds No. | R₁ | R₂ | R₃ | R₅ | R₈ | R₉ | Salt; m.p. °C.; MH⁺; tr (method) |
|---|---|---|---|---|---|---|---|
| 65 (g) | 3-methyl-phenyl-CN | H | —CH₃ | —OCH₃ | H | F | —; 114; 477; 9.3 (method B) |
| 66 (g) | —CH₂-(3-CF₃-phenyl) | H | —CH₃ | —OCH₃ | H | F | —; 60; 534; 10.3 (method B) |
| 67 (a) | 3-methyl-phenyl-CN | H | —CH₃ | Br | Cl | Cl | —; 108; 573; 11 (method B) |
| 68 (c) | —CH₂-(2-F-phenyl) | H | —CH₂CH₃ | Br | Cl | Cl | —; 69; 596; 11.6 (method B) |
| 69 (c) | —CH₂-(4-F-phenyl) | H | —CH₂CH₃ | Br | Cl | Cl | —; 76; 596; 11.3 (method B) |
| 70 (c) | 5-methyl-2-Br-thienyl | H | —CH₂CH₃ | Br | Cl | Cl | —; 143; 648; 18.9 (method B) |
| 71 (c) | 5-methyl-thienyl-isoxazole | H | —CH₂CH₃ | Br | Cl | Cl | —; 143; 648; 18.9 (method B) |
| 72 | 3-Cl-phenyl-methyl | —CH₃ | —CH₂CH₃ | Br | Cl | Cl | —; 78; 612; 12.8 (method B) |

TABLE 1-continued
(I)
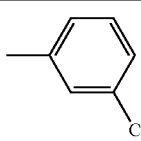
| Compounds No. | R₁ | R₂ | R₃ | R₅ | R₈ | R₉ | Salt; m.p. ° C.; MH⁺; tr (method) |
|---|---|---|---|---|---|---|---|
| 73 (h) | 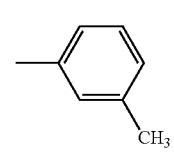 | H | —CH₃ | —OCH₃ | Cl | Cl | — 173; 536; 10.8 (method B) |
| 74 (h) | 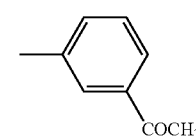 | H | —CH₃ | —OCH₃ | Cl | Cl | — 155; 516; 10.6 (method B) |
| 75 (h) | 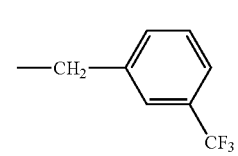 | H | —CH₃ | —OCH₃ | Cl | Cl | — 118; 544; 10 (method B) |
| 76 (h) | 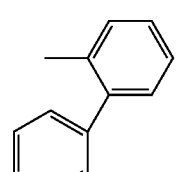 | H | —CH₃ | —OCH₃ | Cl | Cl | — 78; 584; 11 (method B) |
| 77 (h) | 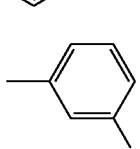 | H | —CH₃ | —OCH₃ | Cl | Cl | — 80; 578; 11.5 (method B) |
| 78 (i) | 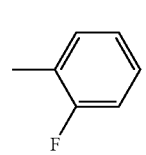 | H | —CH₃ | —OCH₃ | F | F | — — 504; 10.1 (method B) |
| 79 (i) |  | H | —CH₃ | —OCH₃ | F | F | — — 488; 9.6 (method B) |

TABLE 1-continued

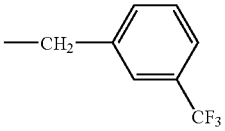

| Compounds No. | $R_1$ | $R_2$ | $R_3$ | $R_5$ | $R_8$ | $R_9$ | Salt; m.p. ° C.; $MH^+$; tr (method) |
|---|---|---|---|---|---|---|---|
| 80 (i) | —CH$_2$—C$_6$H$_4$—CF$_3$ | H | —CH$_3$ | —OCH$_3$ | F | F | — 69 552; 10.41 (method B) |

$R_4$ = H;
$R_6$ = H;
$R_7$ = H;
(a) Compound prepared according to the procedure described in Example 1 from the compound obtained in Preparation 4.1 and the corresponding compound of formula (III).
(b) Compound prepared according to the procedure described in Example 1 from the compound obtained in Preparation 4.2 and the corresponding compound of formula (III).
(c) Compound prepared according to the procedure described in Example 1 from the compound obtained in Preparation 4.3 and the corresponding compound of formula (III).
(d) Compound prepared according to the procedure described in Example 1 from the compound obtained in Preparation 4.4 and the corresponding compound of formula (III).
(e) Compound prepared according to the procedure described in Example 1 from the compound obtained in Preparation 4.5 and the corresponding compound of formula (III).
(f) Compound prepared according to the procedure described in Example 1 from the compound obtained in Preparation 4.6 and the corresponding compound of formula (III).
(g) Compound prepared according to the procedure described in Example 1 from the compound obtained in Preparation 4.7 and the corresponding compound of formula (III).
(h) Compound prepared according to the procedure described in Example 1 from the compound obtained in Preparation 4.8 and the corresponding compound of formula (III).
(i) Compound prepared according to the procedure described in Example 1 from the compound obtained in Preparation 4.9 and the corresponding compound of formula (III).

The compounds of formula (I) possess a very good affinity in vitro ($IC_{50} \leq 5 \times 10^{-7}$M) for the $CB_1$ cannabinoid receptors, under the experimental conditions described by M. Rinaldi-Carmona et al. (FEBS Letters, 1994, 350, 240-244).

The antagonist nature of the compounds of formula (I) has been demonstrated by the results obtained in the adenylate-cyclase inhibition models as described in M. Bouaboula et al., J. Biol. Chem., 1995, 270, 13973-13980, M. Rinaldi-Carmona et al., J. Pharmacol. Exp. Ther., 1996, 278, 871-878 and M. Bouaboula et al., J. Biol. Chem., 1997, 272, 22330-22339.

The toxicity of the compounds of formula (I) is compatible with their use as a medicament.

Thus, according to another of its aspects, the subject of the invention is medicaments which comprise a compound of formula (I), or an addition salt of the latter with a pharmaceutically acceptable acid, or alternatively a solvate or a hydrate of the compound of formula (I).

Thus, the compounds according to the invention may be used in humans or animals, in the treatment or the prevention of diseases involving the $CB_1$ cannabinoid receptors.

For example and without limitation, the compounds of formula (I) are useful as psychotropic medicaments, in particular for the treatment of psychiatric disorders including anxiety, depression, mood disorders, insomnia, delirium disorders, obsessive disorders, psychoses in general, schizophrenia, attention deficit hyperactivity disorder (ADHD), in particular in hyperkinetic children (MBD), and for the treatment of disorders linked to the use of psychotropic substances, in particular in the case of a substance abuse and/or of dependence on a substance, including alcohol dependence and nicotine dependence.

The compounds of formula (I) according to the invention may be used as medicaments for the treatment of migraine, stress, diseases of psychosomatic origin, panic attacks, epileptic attacks, motion disorders, in particular dyskinesia or Parkinson's disease, tremors and dystonia.

The compounds of formula (I) according to the invention may also be used as medicaments in the treatment of memory disorders, cognitive disorders, in particular in the treatment of senile dementia, Alzheimer's disease, and in the treatment of attention or vigilance disorders. Furthermore, the compounds of formula (I) may be useful as neuroprotectants, in the treatment of ischemia, cranial traumas and the treatment of neurodegenerative diseases: including chorea, Huntington's chorea, Tourrette's syndrome.

The compounds of formula (I) according to the invention may be used as medicaments in the treatment of pain: neuropathic pain, acute peripheral pain, chronic pain of inflammatory origin.

The compounds of formula (I) according to the invention may be used as medicaments in the treatment of appetite disorders, craving disorders (for sugars, carbohydrates, drugs, alcohol or any appetizing substance) and/or alimentary canal disorders, in particular for the treatment of obesity or of bulimia and for the treatment of type II diabetes or non-insulin-dependent diabetes and for the treatment of dyslipidaemia and of metabolic syndrome. Thus, the compounds of formula (I) according to the invention are useful in the treatment of obesity and of the risks associated with obesity, in particular cardiovascular risks. Furthermore, the compounds of formula (I) according to the invention may be used as medicaments in the treatment of gastrointestinal disorders, diarrhoeal disorders, ulcers, emesis, bladder and urinary disorders, disorders of endocrine origin, cardiovascular disorders, hypotension, hemorrhagic shock, septic shock, chronic cirrhosis of the liver, hepatic steatosis, steatohepatitis, asthma, Raynaud's syndrome, glaucoma, fertility disorders, inflammatory phenomena, immune system diseases, in particular autoimmune and neuroinflammatory diseases such as rheumatoid arthritis, reactive arthritis, diseases causing demyelinization, multiple sclerosis, infectious and viral diseases such as encephalitis, stroke and as medicaments for anticancer therapy, for the treatment of Guillain-Barre syndrome and for the treatment of osteoporosis.

According to the present invention, the compounds of formula (I) are most particularly useful for the treatment of psychotic disorders, in particular schizophrenia, attention deficit hyperactivity disorders (ADHD), in hyperkinetic children (MBD); for the treatment of appetite disorders and obesity; for the treatment of memory and cognitive disorders; for the treatment of alcohol dependence, nicotine dependence, that is to say for withdrawal from alcohol and for smoking cessation.

According to one of its aspects, the present invention relates to the use of a compound of formula (I), of its pharmaceutically acceptable salts and of their solvates or hydrates for the treatment of the disorders and diseases indicated above.

According to another of its aspects, the present invention relates to pharmaceutical compositions comprising, as active ingredient, a compound according to the invention. These pharmaceutical compositions contain an effective dose of at least one compound according to the invention, or a pharmaceutically acceptable salt, a solvate or a hydrate of the said compound, and at least one pharmaceutically acceptable excipient.

The said excipients are chosen according to the pharmaceutical dosage form and the desired mode of administration, from the usual excipients which are known to a person skilled in the art.

In the pharmaceutical compositions of the present invention for oral, sublingual, subcutaneous, intramuscular, intravenous, topical, local, intratracheal, intranasal, transdermal or rectal administration, the active ingredient of formula (I) above, or its possible salt, solvate or hydrate, may be administered in unit form for administration, as a mixture with conventional pharmaceutical excipients, to animals and to human beings for the prophylaxis or the treatment of the disorders or diseases above.

The appropriate unit forms for administration comprise the forms by the oral route such as tablets, soft or hard gelatin capsules, powders, granules and oral solutions or suspensions, the forms for sublingual, buccal, intratracheal, intraocular or intranasal administration, for administration by inhalation, the forms for topical, transdermal, subcutaneous, intramuscular or intravenous administration, the forms for rectal administration and implants. For topical application, it is possible to use the compounds according to the invention in creams, gels, ointments or lotions.

By way of example, a unit form for administration of a compound according to the invention in tablet form may comprise the following compounds:
Compound according to the invention: 50.0 mg
Mannitol: 223.75 mg
Croscarmellose sodium: 6.0 mg
Maize starch: 15.0 mg
Hydroxypropylmethylcellulose: 2.25 mg
Magnesium stearate: 3.0 mg By the oral route, the dose of active ingredient administered per day may be up to 0.01 to 100 mg/kg, in single or divided doses, preferably 0.02 to 50 mg/kg.

There may be specific cases where higher or lower doses are appropriate, such doses do not depart from the scope of the invention. According to the usual practice, the appropriate dose for each patient is determined by the doctor according to the mode of administration, the weight and the response of the said patient.

The present invention, according to another of its aspects, also relates to a method for treating the pathologies indicated above, which comprises the administration, to a patient, of an effective dose of a compound according to the invention, or one of its pharmaceutically acceptable salts or hydrates or solvates.

What is claimed is:

1. A compound corresponding to formula (I):

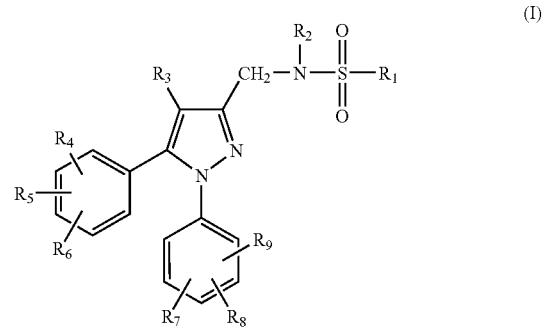

wherein:
$R_1$ represents
a $(C_1-C_6)$alkyl;
a $(C_3-C_7)$cycloalkyl which is unsubstituted or substituted once or several times with a $(C_1-C_3)$alkyl group;
a $(C_3-C_7)$cycloalkylmethyl which is unsubstituted or substituted once or several times on the carbocycle with a $(C_1-C_3)$alkyl;
a phenyl which is unsubstituted or mono-, di- or trisubstituted with a substituent independently chosen from a halogen atom, a $(C_1-C_4)$alkyl, a $(C_1-C_3)$ alkoxy, a cyano, a trifluoromethyl radical, a trifluoromethoxy radical, an $S(O)_n$Alk group, a $(C_1-C_3)$ alkylcarbonyl group, a phenyl;

a benzyl which is unsubstituted or mono- or disubstituted with a substituent independently chosen from a halogen atom, a $(C_1-C_3)$alkyl, a $(C_1-C_3)$alkoxy; a trifluoromethyl radical;

a thienyl which is unsubstituted or substituted with a halogen atom or with an isoxazolyl;

$R_2$ represents a hydrogen atom or a $(C_1-C_3)$alkyl;

$R_3$ represents a hydrogen atom or a $(C_1-C_5)$alkyl;

$R_4$, $R_5$, $R_6$, $R_7$, $R_8$ and $R_9$ each independently represent a hydrogen atom, a halogen atom, a $(C_1-C_7)$alkyl, a $(C_1-C_5)$alkoxy, a trifluoromethyl radical or an $S(O)_n$Alk group;

n represents 0, 1 or 2; and

Alk represents a $(C_1-C_4)$alkyl; or a salt, a hydrate or a solvate thereof.

2. The compound of formula (I) as claimed in claim 1, wherein:

$R_1$ represents ethyl, isopropyl or n-butyl;

cyclohexyl;

cyclohexylmethyl;

2-chlorophenyl, 3-chlorophenyl, 2-fluorophenyl, 3-chloro-4-fluorophenyl, 4-bromo-2-ethylphenyl, 3-methylphenyl, 4-tert-butylphenyl, 3,5-dimethylphenyl, 3-methoxyphenyl, 4-methoxyphenyl, 3-cyanophenyl, 4-cyanophenyl, 2-(trifluoromethyl)phenyl, 3-(trifluoromethyl)phenyl, 4-(trifluoromethyl)phenyl, 3,5-bis(trifluoromethyl)phenyl, 2-(trifluoromethoxy)phenyl, 3-(trifluoromethoxy)phenyl, 2-(methylsulfonyl)phenyl, 3-(methylsulfonyl)phenyl, 3-acetylphenyl, 3-biphenyl or 2-biphenyl;

3-chlorobenzyl, 2-fluorobenzyl, 4-fluorobenzyl, 3-(trifluoromethyl)benzyl or 4-(trifluoromethyl)benzyl;

5-bromo-2-thienyl or 5-isoxazol-3-yl-2-thienyl;

$R_2$ represents hydrogen or methyl;

$R_3$ represents methyl or ethyl;

$R_4$ represents hydrogen;

$R_5$ is at the 4-position of the phenyl and represents bromine, chlorine or fluorine, or methoxy;

$R_6$ represents hydrogen;

$R_7$ represents hydrogen;

$R_8$ is at the 4-position of the phenyl and represents hydrogen, chlorine or fluorine; and $R_9$ is at the 2-position of the phenyl and represents chlorine or fluorine; or a salt, a hydrate or a solvate thereof.

3. The compound of formula (I) as claimed in claim 1, chosen from:

N-[[5-(4-bromophenyl)-1-(2,4-dichlorophenyl)-4-methyl-1H-pyrazol-3-yl]methyl]butane-1-sulfonamide;

N-[[5-(4-bromophenyl)-1-(2,4-dichlorophenyl)-4-methyl-1H-pyrazol-3-yl]methyl]-cyclohexanesulfonamide;

N-[[5-(4-bromophenyl)-1-(2,4-dichlorophenyl)-4-methyl-1H-pyrazol-3-yl]methyl]-cyclohexylmethanesulfonamide;

N-[[5-(4-bromophenyl)-1-(2,4-dichlorophenyl)-4-methyl-1H-pyrazol-3-yl]methyl]-3-chlorobenzenesulfonamide;

N-[[5-(4-bromophenyl)-1-(2,4-dichlorophenyl)-4-methyl-1H-pyrazol-3-yl]methyl]-4-tert-butylbenzenesulfonamide;

N-[[5-(4-bromophenyl)-1-(2,4-dichlorophenyl)-4-methyl-1H-pyrazol-3-yl]methyl]-3-methoxybenzenesulfonamide;

N-[[5-(4-bromophenyl)-1-(2,4-dichlorophenyl)-4-methyl-1H-pyrazol-3-yl]methyl]-4-methoxybenzenesulfonamide;

N-[[5-(4-bromophenyl)-1-(2,4-dichlorophenyl)-4-methyl-1H-pyrazol-3-yl]methyl]-4-(trifluoromethyl)benzenesulfonamide;

N-[[5-(4-bromophenyl)-1-(2,4-dichlorophenyl)-4-methyl-1H-pyrazol-3-yl]methyl]-2-(methylsulfonyl)benzenesulfonamide;

N-[[5-(4-bromophenyl)-1-(2,4-dichlorophenyl)-4-methyl-1H-pyrazol-3-yl]methyl]-1-(3-chlorophenyl)methanesulfonamide;

N-[[5-(4-bromophenyl)-1-(2,4-dichlorophenyl)-4-methyl-1H-pyrazol-3-yl]methyl]-1-[3-(trifluoromethyl)phenyl]methanesulfonamide;

N-[[5-(4-bromophenyl)-1-(2,4-dichlorophenyl)-4-methyl-1H-pyrazol-3-yl]methyl]-3-chloro-4-fluorobenzenesulfonamide;

N-[[5-(4-chlorophenyl)-1-(2,4-dichlorophenyl)-4-methyl-1H-pyrazol-3-yl]methyl]-butane-1-sulfonamide;

3-chloro-N-[[5-(4-chlorophenyl)-1-(2,4-dichlorophenyl)-4-methyl-1H-pyrazol-3-yl]methyl]benzenesulfonamide;

4-tert-butyl-N-[[5-(4-chlorophenyl)-1-(2,4-dichlorophenyl)-4-methyl-1H-pyrazol-3-yl]methyl]benzenesulfonamide;

N-[[5-(4-chlorophenyl)-1-(2,4-dichlorophenyl)-4-methyl-1H-pyrazol-3-yl]methyl]-3-methoxybenzenesulfonamide;

N-[[5-(4-chlorophenyl)-1-(2,4-dichlorophenyl)-4-methyl-1H-pyrazol-3-yl]methyl]-3-cyanobenzenesulfonamide;

N-[[5-(4-chlorophenyl)-1-(2,4-dichlorophenyl)-4-methyl-1H-pyrazol-3-yl]methyl]-4-(trifluoromethyl)benzenesulfonamide;

N-[[5-(4-chlorophenyl)-1-(2,4-dichlorophenyl)-4-methyl-1H-pyrazol-3-yl]methyl]-2-(trifluoromethoxy)benzenesulfonamide;

N-[[5-(4-chlorophenyl)-1-(2,4-dichlorophenyl)-4-methyl-1H-pyrazol-3-yl]methyl]-2-(methylsulfonyl)benzenesulfonamide;

3-chloro-N-[[5-(4-chlorophenyl)-1-(2,4-dichlorophenyl)-4-methyl-1H-pyrazol-3-yl]methyl]-4-fluorobenzenesulfonamide;

4-bromo-N-[[5-(4-chlorophenyl)-1-(2,4-dichlorophenyl)-4-methyl-1H-pyrazol-3-yl]methyl]-2-ethylbenzenesulfonamide;

N-[[5-(4-bromophenyl)-1-(2,4-dichlorophenyl)-4-ethyl-1H-pyrazol-3-yl]methyl]ethanesulfonamide;

N-[[5-(4-bromophenyl)-1-(2,4-dichlorophenyl)-4-ethyl-1H-pyrazol-3-yl]methyl]propane-2-sulfonamide;

N-[[5-(4-bromophenyl)-1-(2,4-dichlorophenyl)-4-ethyl-1H-pyrazol-3-yl]methyl]butane-1-sulfonamide;

N-[[5-(4-bromophenyl)-1-(2,4-dichlorophenyl)-4-ethyl-1H-pyrazol-3-yl]methyl]-cyclohexanesulfonamide;

N-[[5-(4-bromophenyl)-1-(2,4-dichlorophenyl)-4-ethyl-1H-pyrazol-3-yl]methyl]-1-cyclohexylmethanesulfonamide;

N-[[5-(4-bromophenyl)-1-(2,4-dichlorophenyl)-4-ethyl-1H-pyrazol-3-yl]methyl]-3-chlorobenzenesulfonamide;

N-[[5-(4-bromophenyl)-1-(2,4-dichlorophenyl)-4-ethyl-1H-pyrazol-3-yl]methyl]-2-chlorobenzenesulfonamide;

N-[[5-(4-bromophenyl)-1-(2,4-dichlorophenyl)-4-ethyl-1H-pyrazol-3-yl]methyl]-3-methylbenzenesulfonamide;

N-[[5-(4-bromophenyl)-1-(2,4-dichlorophenyl)-4-ethyl-1H-pyrazol-3-yl]methyl]-4-tert-butylbenzenesulfonamide;

N-[[5-(4-bromophenyl)-1-(2,4-dichlorophenyl)-4-ethyl-1H-pyrazol-3-yl]methyl]-4-methoxybenzenesulfonamide;

N-[[5-(4-bromophenyl)-1-(2,4-dichlorophenyl)-4-ethyl-1H-pyrazol-3-yl]methyl]-3-methoxybenzenesulfonamide;

N-[[5-(4-bromophenyl)-1-(2,4-dichlorophenyl)-4-ethyl-1H-pyrazol-3-yl]methyl]-4-(trifluoromethyl)benzenesulfonamide;

N-[[5-(4-bromophenyl)-1-(2,4-dichlorophenyl)-4-ethyl-1H-pyrazol-3-yl]methyl]-3-(trifluoromethyl)benzenesulfonamide;

N-[[5-(4-bromophenyl)-1-(2,4-dichlorophenyl)-4-ethyl-1H-pyrazol-3-yl]methyl]-2-(trifluoromethyl)benzenesulfonamide;

N-[[5-(4-bromophenyl)-1-(2,4-dichlorophenyl)-4-ethyl-1H-pyrazol-3-yl]methyl]-3-(trifluoromethoxy)benzenesulfonamide;

N-[[5-(4-bromophenyl)-1-(2,4-dichlorophenyl)-4-ethyl-1H-pyrazol-3-yl]methyl]-2-(trifluoromethoxy)benzenesulfonamide;

3-acetyl-N-[[5-(4-bromophenyl)-1-(2,4-dichlorophenyl)-4-ethyl-1H-pyrazol-3-yl]methyl]benzenesulfonamide;

N-[[5-(4-bromophenyl)-1-(2,4-dichlorophenyl)-4-ethyl-1H-pyrazol-3-yl]methyl]biphenyl-3-sulfonamide;

N-[[5-(4-bromophenyl)-1-(2,4-dichlorophenyl)-4-ethyl-1H-pyrazol-3-yl]methyl]-1-[4-(trifluoromethyl)phenyl]methanesulfonamide;

N-[[5-(4-bromophenyl)-1-(2,4-dichlorophenyl)-4-ethyl-1H-pyrazol-3-yl]methyl]-1-[3-(trifluoromethyl)phenyl]methanesulfonamide;

N-[[5-(4-bromophenyl)-1-(2,4-dichlorophenyl)-4-ethyl-1H-pyrazol-3-yl]methyl]-3,5-dimethylbenzenesulfonamide;

N-[[5-(4-bromophenyl)-1-(2,4-dichlorophenyl)-4-ethyl-1H-pyrazol-3-yl]methyl]-3,5-bis(trifluoromethyl)benzenesulfonamide;

3-chloro-N-[[1-(2-chlorophenyl)-5-(4-chlorophenyl)-4-methyl-1H-pyrazol-3-yl]methyl]benzenesulfonamide;

N-[[1-(2-chlorophenyl)-5-(4-chlorophenyl)-4-methyl-1H-pyrazol-3-yl]methyl]-2-fluorobenzenesulfonamide;

N-[[1-(2-chlorophenyl)-5-(4-chlorophenyl)-4-methyl-1H-pyrazol-3-yl]methyl]-3-cyanobenzenesulfonamide;

N-[[1-(2-chlorophenyl)-5-(4-chlorophenyl)-4-methyl-1H-pyrazol-3-yl]methyl]-3-methoxybenzenesulfonamide;

N-[[5-(4-bromophenyl)-1-(2,4-dichlorophenyl)-4-methyl-1H-pyrazol-3-yl]methyl]-3-methoxybenzenesulfonamide;

N-[[5-(4-bromophenyl)-1-(2,4-dichlorophenyl)-4-methyl-1H-pyrazol-3-yl]methyl]-3-cyanobenzenesulfonamide;

N-[[5-(4-bromophenyl)-1-(2,4-dichlorophenyl)-4-ethyl-1H-pyrazol-3-yl]methyl]-1-(2-fluorophenyl)methanesulfonamide;

N-[[5-(4-bromophenyl)-1-(2,4-dichlorophenyl)-4-ethyl-1H-pyrazol-3-yl]methyl]-1-(4-fluorophenyl)methanesulfonamide;

5-bromo-N-[[5-(4-bromophenyl)-1-(2,4-dichlorophenyl)-4-ethyl-1H-pyrazol-3-yl]methyl]thiophene-2-sulfonamide;

N-[[5-(4-bromophenyl)-1-(2,4-dichlorophenyl)-4-ethyl-1H-pyrazol-3-yl]methyl]-5-isoxazol-3-ylthiophene-2-sulfonamide;

3-chloro-N-[[1-(2,4-dichlorophenyl)-5-(4-methoxyphenyl)-4-methyl-1H-pyrazol-3-yl]methyl]benzenesulfonamide; and N-[[1-(2,4-dichlorophenyl)-5-(4-methoxyphenyl)-4-methyl-1H-pyrazol-3-yl]methyl]-3-methylbenzenesulfonamide; or a salt, a hydrate or a solvate thereof.

4. A method for preparing a compound of formula (I) as claimed in claim 1, comprising:

reacting a compound of formula:

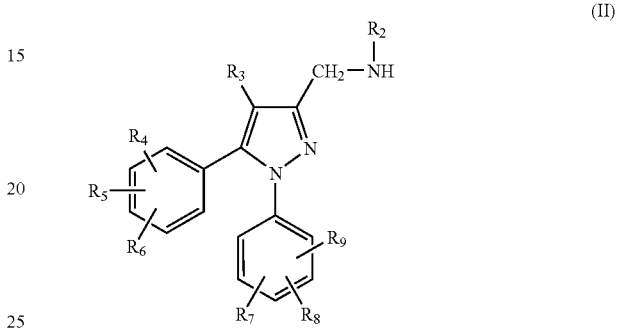

wherein $R_2$, $R_3$, $R_4$, $R_5$, $R_6$, $R_7$, $R_8$ and $R_9$ are as defined for a compound of formula (I) in claim 1, in the presence of a base and in a solvent, with a sulfonyl halide of formula:

wherein $R_1$ is as defined for a compound of formula (I) in claim 1 and Hal represents a halogen atom.

5. A pharmaceutical composition comprising a compound of formula (I) according to claim 1, or a pharmaceutically acceptable salt, a hydrate or a solvate thereof, in combination with at least one pharmaceutically acceptable excipient.

6. The composition according to claim 5, wherein compound of formula (I) is having:

$R_1$ represents
  ethyl, isopropyl or n-butyl;
  cyclohexyl;
  cyclohexylmethyl;
  2-chlorophenyl, 3-chlorophenyl, 2-fluorophenyl, 3-chloro-4-fluorophenyl, 4-bromo-2-ethylphenyl, 3-methylphenyl, 4-tert-butylphenyl, 3,5-dimethylphenyl, 3-methoxyphenyl, 4-methoxyphenyl, 3-cyanophenyl, 4-cyanophenyl, 2-(trifluoromethyl)phenyl, 3-(trifluoromethyl)phenyl, 4-(trifluoromethyl)phenyl, 3,5-bis(trifluoromethyl)phenyl, 2-(trifluoromethoxy)phenyl, 3-(trifluoromethoxy)phenyl, 2-(methylsulfonyl)phenyl, 3-(methylsulfonyl)phenyl, 3-acetylphenyl, 3-biphenyl or 2-biphenyl;
  3-chlorobenzyl, 2-fluorobenzyl, 4-fluoro-benzyl, 3-(trifluoromethyl)benzyl or 4-(trifluoromethyl)benzyl;
  5-bromo-2-thienyl or 5-isoxazol-3-yl-2-thienyl;

$R_2$ represents hydrogen or methyl;

$R_3$ represents methyl or ethyl;

$R_4$ represents hydrogen;

$R_5$ is at the 4-position of the phenyl and represents bromine, chlorine or fluorine, or methoxy;

$R_6$ represents hydrogen;

$R_7$ represents hydrogen;

$R_8$ is at the 4-position of the phenyl and represents hydrogen, chlorine or fluorine; and $R_9$ is at the 2-position of the phenyl and represents chlorine or fluorine.

* * * * *